(12) United States Patent
Pujol et al.

(10) Patent No.: US 11,340,208 B2
(45) Date of Patent: May 24, 2022

(54) METHOD AND APPARATUS FOR ANALYZING A ROCK SAMPLE

(71) Applicant: TOTAL SE, Courbevoie (FR)

(72) Inventors: Ghislain Pujol, Pau (FR); Regis Brugidou, Pau (FR); Pierre Faurissoux, Pau (FR)

(73) Assignee: TOTAL SE, Courbevoie (FR)

( * ) Notice: Subject to any disclaimer, the term of this patent is extended or adjusted under 35 U.S.C. 154(b) by 5 days.

(21) Appl. No.: 16/963,802

(22) PCT Filed: Jan. 23, 2018

(86) PCT No.: PCT/IB2018/000271
§ 371 (c)(1),
(2) Date: Jul. 21, 2020

(87) PCT Pub. No.: WO2019/145745
PCT Pub. Date: Aug. 1, 2019

(65) Prior Publication Data
US 2021/0055279 A1   Feb. 25, 2021

(51) Int. Cl.
*G01N 33/24*   (2006.01)
(52) U.S. Cl.
CPC ......... *G01N 33/241* (2013.01); *G01N 33/246* (2013.01)
(58) Field of Classification Search
CPC .................... G01N 33/241; G01N 33/246
See application file for complete search history.

(56) References Cited

U.S. PATENT DOCUMENTS

| | | | | |
|---|---|---|---|---|
| 2,345,535 | A | * | 3/1944 | Horner ................. G01N 15/088 73/38 |
| 5,493,226 | A | * | 2/1996 | Honarpour ............ E21B 49/005 324/376 |
| 5,679,885 | A | | 10/1997 | Roland et al. |
| 5,698,791 | A | * | 12/1997 | Lemaire ............... G01N 33/241 73/861.04 |
| 5,979,223 | A | * | 11/1999 | Fleury ................. G01N 33/241 73/38 |
| 6,453,727 | B1 | * | 9/2002 | Lenormand ............ G01N 15/08 73/38 |

(Continued)

FOREIGN PATENT DOCUMENTS

CN      205620387 U    10/2016

OTHER PUBLICATIONS

Arnott, "Observations Relating to the Wettability of Porous Rock," Petroleum Transactions, AIME (Year: 1960).*

(Continued)

*Primary Examiner* — John Fitzgerald
(74) *Attorney, Agent, or Firm* — Knobbe, Martens, Olson & Bear, LLP

(57) ABSTRACT

The invention relates to a method of analyzing a rock sample, comprising:—placing a rock sample (2) containing a first fluid into a cell (1);—feeding the cell (1) with at least one second fluid and withdrawing said second fluid from the cell (1), leaving the rock sample (2) immersed in the second fluid; and—measuring an amount of first fluid spontaneously released from the rock sample (2). The invention also relates to an apparatus adapted for implementing this method.

20 Claims, 1 Drawing Sheet

(56) References Cited

U.S. PATENT DOCUMENTS

| | | | |
|---|---|---|---|
| 8,024,960 B2* | 9/2011 | Fleury | G01N 33/241 |
| | | | 73/38 |
| 8,768,628 B2 | 7/2014 | Shawket et al. | |
| 8,939,015 B2* | 1/2015 | Anderson | G01N 33/24 |
| | | | 73/38 |
| 10,167,719 B2* | 1/2019 | Ezzat | G01N 33/24 |
| 10,416,063 B2* | 9/2019 | Gao | G01R 33/5608 |
| 10,677,706 B2* | 6/2020 | McCarty | C09K 8/88 |
| 10,815,416 B2* | 10/2020 | Jin | E21B 43/267 |
| 10,845,291 B2* | 11/2020 | Kanj | G01N 33/241 |
| 10,908,063 B2* | 2/2021 | Gmira | G01N 13/02 |
| 10,995,260 B2* | 5/2021 | Piri | C09K 8/04 |
| 11,073,464 B2* | 7/2021 | Gao | G01R 33/48 |
| 2005/0240360 A1* | 10/2005 | Fleury | G01N 15/0826 |
| | | | 702/50 |
| 2009/0126462 A1 | 5/2009 | Fleury et al. | |
| 2012/0151998 A1* | 6/2012 | Willberg | G01N 1/286 |
| | | | 73/38 |
| 2012/0241149 A1* | 9/2012 | Chen | G01V 3/32 |
| | | | 166/250.01 |
| 2015/0354352 A1* | 12/2015 | Ezzat | G01N 33/24 |
| | | | 73/152.05 |
| 2016/0024372 A1 | 1/2016 | Nariman | |
| 2018/0335374 A1* | 11/2018 | Kanj | G01N 15/0826 |
| 2019/0094120 A1* | 3/2019 | Gmira | G01N 33/24 |
| 2019/0360908 A1* | 11/2019 | Gao | G01N 15/082 |
| 2020/0271563 A1* | 8/2020 | Chen | G01N 15/0806 |
| 2020/0371011 A1* | 11/2020 | Chen | G01N 33/246 |
| 2021/0002543 A1* | 1/2021 | Jin | C09K 8/602 |

OTHER PUBLICATIONS

Morrow et al. "Characterization of Wettability from Spontaneous Imbibition Measurements," Petroleum Society of CIM & ACSTRA (Year: 1994).*

Petroleum Development Laboratory, Univ. of Alaska Fairbanks "Characterization and Alteration of Wettability States of Alaskan Reservoirs to Improve Oil Recovery Efficiency" Office of Fossil Energy (Year: 2008).*

Robin, "Interfacial Phenomena: Reservoir Wettability in Oil Recovery," Oil & Gas Science and Technology, Vo. 56, No. 1 (Year: 2001).*

Search Report and Written Opinion in International Application No. PCT/IB2018/000271, dated Oct. 18, 2018, in 12 pages.

* cited by examiner

METHOD AND APPARATUS FOR ANALYZING A ROCK SAMPLE

TECHNICAL FIELD

The present invention relates to a method of analyzing a rock sample and an apparatus for implementing said method.

TECHNICAL BACKGROUND

Hydrocarbons (such as crude oil) are extracted form a subterranean formation (or reservoir) by means of one or more production wells drilled in the reservoir. Before production begins, the formation, which is a porous medium, is saturated with hydrocarbons.

The initial recovery of hydrocarbons is generally carried out by techniques of "primary recovery", in which only the natural forces present in the reservoir are relied upon. In this primary recovery, only part of the hydrocarbons is ejected from the pores by the pressure of the formation. Typically, once the natural forces are exhausted and primary recovery is completed, there is still a large volume of hydrocarbons left in the reservoir, generally more than two thirds.

This phenomenon has led to the development of enhanced oil recovery (EOR) techniques. Many of such EOR techniques rely on the injection of a fluid into the reservoir in order to produce an additional quantity of hydrocarbons. The fluid used can in particular be an aqueous solution, such as brine (optionally in combination with chemicals), which is injected via one or more injection wells.

In order to optimize hydrocarbon recovery in such a case, it is useful to determine the wettability of the reservoir's rock by an aqueous solution intended to be used as an injection fluid.

The Amott test is a classical method for performing a preliminary study of wettability. It involves the measurement of the amount of fluid spontaneously and forcibly imbibed by a rock sample. To this end, an oil saturated rock sample is placed in an aqueous solution. The aqueous solution spontaneously penetrates the sample and expels some of the oil, which separates due to its immiscibility with water. The measurement of the volume of released oil is indicative of so-called spontaneous imbibition. The sample is then placed in a centrifuge. More oil is thus released. The volume of oil released owing to centrifugation is indicative of so-called forced imbibition. The same steps are then carried out on in a reverse manner by performing spontaneous drainage followed by forced drainage of the sample by oil.

A more precise but much more complex and costly method of analysis relies on a sweeping test performed on a core sample, which involves continuously passing an injection fluid through the sample under pressure, collecting and analyzing output fluid, and performing imaging along the sample.

Usually, the Amott test is performed as a preliminary test, and the sweeping test is conducted only when a more complete and accurate assessment of the expected efficacy of hydrocarbon recovery is needed.

There is currently a need to improve the preliminary wettability study of a rock sample.

SUMMARY OF THE INVENTION

It is a first object of the invention to provide a method of analyzing a rock sample, comprising:

placing a rock sample containing a first fluid into a cell;
feeding the cell with at least one second fluid and withdrawing said second fluid from the cell, leaving the rock sample immersed in the second fluid; and
measuring an amount of first fluid spontaneously released from the rock sample.

According to some embodiments, the second fluid is continuously fed to the cell and continuously withdrawn from the cell.

According to some embodiments, use is made of a single second fluid.

According to some embodiments, the method comprises successively feeding the cell with a second fluid and withdrawing said second fluid from the cell, and then feeding the cell with another second fluid and withdrawing said other second fluid from the cell.

According to some embodiments, the first fluid spontaneously released from the rock sample is collected in a collection area of the cell and the volume of first fluid in the collection area is measured.

According to some embodiments, the first fluid in the collection area has a surface which is in contact with a gas, and the position of the first fluid in the collection area is set at a target position by adjusting gas pressure.

According to some embodiments, the second fluid or each second fluid is an aqueous solution, and the first fluid is oil.

According to some embodiments, the second fluid is oil, and the first fluid is an aqueous solution.

According to some embodiments, the method further comprises removing adsorbed first fluid at the surface of the rock sample, preferably intermittently.

According to some embodiments, the method further comprises scraping the rock sample inside the cell, preferably intermittently.

According to some embodiments, the second fluid and rock sample in the cell are maintained at an absolute pressure of from 2 to 10 bar.

According to some embodiments, the second fluid and rock sample in the cell are maintained at a temperature of from 25 to 150° C., preferably from 40 to 120° C. and more preferably from 60 to 110° C.

It is another object of the invention to provide an apparatus for analyzing a rock sample containing a first fluid, comprising:

a cell for accommodating the rock sample;
a feed line for feeding the cell with a second fluid;
an output line for withdrawing said second fluid from the cell; and
a measurement system for measuring the amount of first fluid spontaneously released from the rock sample.

According to some embodiments, the apparatus comprises a pressure regulation system for maintaining pressure in the cell and rock sample at a predetermined level.

According to some embodiments, the cell comprises a collection area, and the measurement system is configured for measuring a volume of first fluid in the collection area.

According to some embodiments, the cell comprises a first portion for accommodating the rock sample and a second portion as the collection area, wherein the second portion is a generally vertical tubular portion, having a reduced horizontal cross-section relative to the first portion.

According to some embodiments, the collection area is located in a top part of the cell, and the apparatus further comprises a gas line for bringing gas in contact with the first fluid in the collection area, the gas line being provided with gas pressure adjustment equipment.

According to some embodiments, the collection area is located in a bottom part of the cell.

According to some embodiments, the apparatus comprises a holder for the rock sample in the cell, said holder being preferably a rotating holder.

According to some embodiments, the apparatus comprises one more scrapers for scraping the rock sample in the cell, which are preferably in a fixed position in the cell.

According to some embodiments, the apparatus comprises an oven in which the cell is placed.

According to some embodiments, the apparatus comprises an oven in which a plurality of cells are placed.

The present invention addresses the need expressed above. In particular the invention provides an improved method of preliminarily analyzing the wettability of a rock sample. Owing to the invention, information on wettability and recovery depending on fluid composition can be obtained. The invention makes it possible to screen different fluids in similar conditions and to identify which ones achieves the best oil recovery. This screening makes it possible to reduce the experimental cost and time to select appropriate fluid for a sweeping experiment.

This is achieved by providing a cell into which a rock sample containing a first fluid (e.g. oil) is placed, feeding the cell with a second fluid (e.g. an aqueous solution) and withdrawing said second fluid from the cell, and measuring an amount of first fluid spontaneously released from the rock sample.

Contrary to the classical setup used for measuring spontaneous release of fluid from a rock sample in the Amott test, which is closed, the present invention relies on an open system, where fluid circulates into and out of the cell during the analysis.

According to some embodiments, the invention has one or preferably several of the following advantageous features:
- Fresh second fluid (e.g. aqueous solution) is fed to the cell during the analysis, which makes it possible to keep the fluid under constant conditions, in particular at a constant pH, and overall in conditions which are well representative of in situ conditions.
- The analysis may be performed at a relatively high temperature equal or close to the temperature of the reservoir, in order to better assess the wettability of the rock in situ. This is made possible due to the pressure applied within the cell, so as to avoid any degassing.
- Adsorbed first fluid (e.g. oil), in particular released first fluid, at the surface of the rock sample (notably due to the wettability or rugosity of the sample) can artificially reduce the amount of first fluid spontaneously released from the rock sample and make the measurement less accurate. Removing such adsorbed fluid, for instance by scraping the surface of the sample, thus improves the efficiency and accuracy of the analysis.
- According to the invention, it is possible to sequentially test two or more second fluids (e.g. aqueous solutions) in order to maximize the spontaneous release of first fluid (e.g. oil) from the rock sample.
- The method of the invention may be quicker than the method of the prior art, due to the combined effect of high temperature, removal of adsorbed fluid from the sample and feeding of fresh fluid.

Fluids can be trapped within a rock sample due to capillary forces. A fraction of such fluids contained in the rock sample may not be extracted by conventional methods, such as centrifugation. Owing to the invention, capillary forces, as well as the wettability of the rock, can be modified so as to increase fluid recovery.

DESCRIPTION OF EMBODIMENTS

The invention will now be described in more detail without limitation in the following description.

Figure 1:
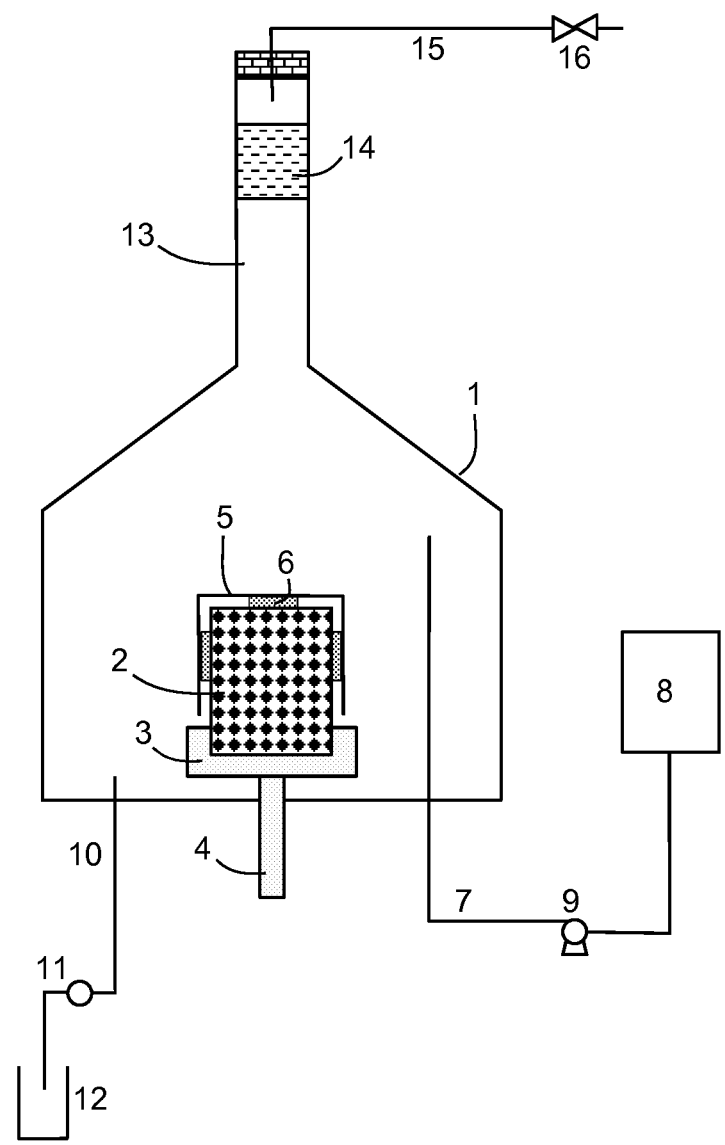
FIG. 1 schematically shows an apparatus according to one embodiment of the invention.

Making reference to FIG. 1, the apparatus of the invention may comprise a cell 1, in which a rock sample 2 is placed. The rock sample 2 may be supported by a holder 3. It may also be (firmly) fixed, e.g. press-fit, to the holder 3. The rock sample 2 may for instance be a generally cylindrical block of rock, the axis of the cylinder being oriented vertically in the cell 1.

A feed line 7 may be provided for feeding a fluid (called second fluid) from a source 8 to the cell 1. A pump 9 may be provided on the feed line 7 to force the second fluid to flow into the cell 1. The second fluid is immiscible with the first fluid.

An output line 10 may also be provided to withdraw said fluid from the cell 1. The output line 10 may send the withdrawn fluid to a disposal area 12. A pressure regulation system 11 may be provided to regulate pressure within the cell 1. By way of example, the pressure regulation system 11 may include a backpressure regulator provided on the output line 10.

During the analysis of the rock sample 2 in the apparatus, fluid contained in the sample (called first fluid) is spontaneously released from the sample 2. The apparatus may comprise a measurement system for measuring the amount of first fluid spontaneously released from the sample 2.

In particular, the cell 1 may include a collection area 13 for collecting the released first fluid.

The cell 1 may include a first portion and a second portion. The rock sample 2 is placed in the first portion, and the second portion is the collection area 13. In the embodiment illustrated on the drawing, the first portion is the bottom portion, and the second portion (collection area 13) is the top portion.

The second portion or collection area 13 may be a generally elongated, vertical-oriented portion. Its horizontal cross-section may be smaller than that of the first portion.

By way of example, the first portion may have a tubular shape having a length from 30 to 120 mm, preferably from 50 to 90 mm, more preferably from 60 to 80 mm. If the cross-section of the first portion is circular, it may have a diameter from 30 to 100 mm, preferably from 40 to 80 mm, more preferably from 50 to 60 mm.

By way of example, the second portion may have a tubular shape having a length from 50 to 250 mm, preferably from 100 to 180 mm, more preferably from 120 to 160 mm. If the cross-section of the second portion is circular, it may have a diameter from 1 to 30 mm, preferably from 2 to 20 mm, more preferably from 5 to 15 mm.

A transition portion between the first portion and the second portion may be provided if necessary. The transition portion may be tapered from the first portion to the second portion. The height of the transition portion (or distance between the first portion and second portion) may e.g. range from 1 to 60 mm, preferably from 5 to 40 mm, more preferably from 10 to 30 mm.

First fluid (e.g. oil) released from the rock sample 2 may separate from the bulk of the second fluid and accumulate in the collection area 13 as a collected fraction 14. The measurement system may therefore be adapted or configured for measuring the volume of the collected fraction 14. The measurement system may in particular include graduations in the collection area 13. The wall(s) of the collection area 13 may be made of glass or any other transparent material. In some variations, the entire wall(s) of the cell 1 may be made of glass or any other transparent material.

The geometrical shape of the collection area 13 may be adapted so as to provide an accurate measurement. In particular, an elongated tubular shape with a relatively small cross-section makes it possible to accurately determine the volume of the collected fraction 14 by evaluating the height of the collected fraction 14. The measurement system may also include a camera and optionally an image analysis software executed on a computer in order to measure the volume of the collected fraction 14.

In the illustrated embodiment, the vertical position of the collected fraction 14 may vary over time. This may be due for instance to the temperature rising in the cell 1 (e.g. from the ambient temperature to a target elevated temperature), so that the fluids dilate.

In order to keep the collected fraction 14 within the collection area 13 or to keep it within certain desired boundaries in the collection area 13, a gas line 15 is connected in the top part of the cell 1. Gas, preferably inert gas such as nitrogen, is thus fed to the uppermost part of the cell 1 by the gas line 15. A gas/first fluid interface forms in the top part of the cell 1, typically within the collection area 13. Gas pressure adjustment equipment 16 may be provided on the gas line 15. It may include a valve. It makes it possible to set the position of the collected fraction 14 in the collection area 13 or within desired boundaries.

When such gas pressure adjustment equipment 16 is present, it may also be considered as part of the abovementioned pressure regulation system.

Sealing may be provided between the cell 1 and each of the respective feed line 7, output line 10 and gas line 15 in order to prevent any input or output of material to or from the environment.

The holder 3 for the rock sample 2 may be a rotating holder. It may be connected to a spindle 4 driven by a motor located outside of the cell 1.

A frame 5 may be provided around the rock sample 2. This frame 5 may be provided with one or more scrapers 6. The scrapers 6 may be brushes, plates or the like. The frame 5 may be fixed to one of the walls of the cell 1 (not shown on the drawing), preferably the floor of the cell 1. The frame 5 may have an adjustable position (especially a vertically adjustable position) to make sure that the scrapers 6 are in (gentle) contact with the rock sample 2.

With such an arrangement, the scrapers 6 may scrape the surface of the rock sample when the rock sample is rotated owing to the holder 3.

Alternatively, in other embodiments, the holder 3 and the rock sample 2 may be fixed relative to the walls of the cell 1, while the frame 5 and scrapers 6 may move, for instance rotate, relative to the rock sample 2, in order to scrape the surface of the rock sample 2.

Scrapers 6 may be provided for scraping one or more surfaces of the rock sample 2 exposed to the second fluid, such as the top surface and the side surface, if the rock sample 2 is of a cylindrical shape.

Figure 2A:
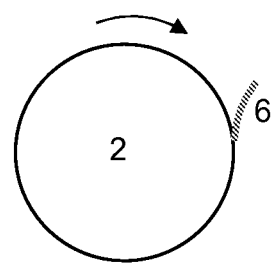
FIGS. 2a and 2b are schematic top views respectively showing scrapers positioned on a rock sample, according to some embodiments.
Figure 2B:
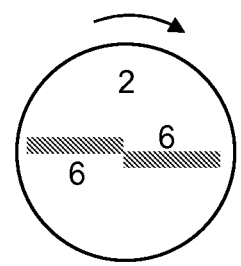

FIGS. 2a and 2b illustrate exemplary configurations for the scrapers 6. In FIG. 2a, a scraper 6 runs vertically along the side of the rock sample 2. More than one such scrapers 6 may be provided. In FIG. 2b, two scrapers 6 are provided on top of the rock sample (only one could also be provided). Each scraper 6 may be made of a sheet of flexible material, one end of which is attached to the frame 5 while the other end contacts the rock sample 2. The scrapers 6 may be slightly compressed against the rock sample in order to gently scrape the surface when the rock sample rotates as illustrated by the arrow. Advantageously, the scrapers 6 illustrated in FIG. 2a and FIG. 2b may be combined.

Alternative features for disrupting first fluid (e.g. oil) adsorbed at the surface of the rock sample 2 may include an agitator for agitating fluid within the cell 1.

The apparatus shown in FIG. 1 is especially useful when the first fluid contained in the rock sample 2 is oil, and the second fluid introduced into the cell 1 is an aqueous solution. Indeed, since oil has a smaller density than an aqueous solution, oil released from the rock sample tends to travel to the top part of the apparatus, where the collection area 13 is located.

The illustrated apparatus may however be easily modified to implement the reverse situation, where the first fluid contained in the rock sample 2 is an aqueous solution, and the second fluid introduced into the cell 1 is oil. In such a case, the apparatus may be arranged upside down relative to the illustrated embodiment. The rock sample 2 may be placed in a top portion of the cell 1. It may for instance be held by the holder 3 from a roof of the cell 1. The collection area 13, which may have the same shape as described above, may be provided in a bottom portion of the cell 1. Since water is denser than oil, the aqueous solution released from the rock sample tends to accumulate as a collected fraction 14 at the very bottom of the cell 1. In such a case, the gas line 15 and gas pressure adjustment equipment 16 may be suppressed, since the position of the collected fraction 14 tends to remain fixed at the very bottom of the cell 1.

A temperature regulation system may be provided in order to regulate the temperature in the cell 1. For instance, the apparatus described above may be placed in an oven (including a temperature sensor) or the apparatus described above may comprise an oven (including a temperature sensor) in which the cell 1 is arranged. The source 8 of second fluid and the pump 9 may be positioned outside the oven.

The apparatus may comprise a plurality of cells 1 and corresponding feed lines 7, output lines 10 and optionally gas lines 15. The plurality of cells 1 may be placed in the same oven and be operated independently from each other. This makes it possible to parallelly test different fluids on similar rock samples.

The above apparatus may be used to implement the method of the invention.

The method of the invention may include measuring an amount of first fluid spontaneously released from a rock sample 2 which is immersed in the second fluid.

The rock sample 2 may be placed into the cell 1. The cell 1 may be fed with a second fluid, and said second fluid may be withdrawn from the cell 1. The feeding flow rate may be substantially equal to the withdrawal flow rate, so that the amount of second fluid in the cell 1 remains substantially constant. The rock sample 2 thus remains immersed in the second fluid.

The feeding flow rate may be adjusted in such a manner that the characteristic time defined as the volume of second fluid contained in the cell 1 divided by the feeding flow rate ranges from 1 cc/h to 120 cc/h, preferably from 50 cc/h to 100 cc/h, and more preferably from 70 cc/h to 90 cc/h.

Absolute pressure within the cell may be set at a desired level, such as from 1 to 20 bar, preferably from 2 to 10 bar. The inflow and outflow of second fluid to and from the cell 1 is preferably continuous. However, in some variations, the inflow and outflow of second fluid may be stopped and resumed. The inflow and outflow of second fluid may thus be intermittent or periodical.

"Spontaneous release" of first fluid from the rock sample 2 means that the first fluid naturally exits the rock sample without being forcibly pushed out of the sample by a pressure differential between one end of the sample and another end of the sample, as may be exerted for instance in a sweeping test. In the present method, pressure is substantially uniform within the cell 1 and notably within the rock sample 2—the pressure difference between the top and bottom of the cell 1 due to the weight of the fluid can be considered as negligible. In other words, pressure of the first fluid within the pores of the rock sample 2 is substantially equal to the pressure of the neighboring second fluid.

First fluid released from the rock sample 2 may be collected in the collection area 13 and the amount of first fluid thus collected may be measured. The amount may be quantified as a volume or a weight, and preferably as a volume. The measurement of the amount of released first fluid may be performed in a continuous manner, or preferably in an intermittent e.g. periodical manner, over the course of the analysis. For instance, the measurement may be performed once an hour, or once every 12 hours, or once a day, while the rock sample 2 remains immersed in the second fluid. The total course of the analysis may be for instance from 1 week to 1 year, preferably from 2 weeks to 6 months, and more preferably from 3 weeks to 2 months.

As the first fluid exits the pores of the rock sample 2, it may tend to primarily or transiently accumulate at the surface of the sample, for instance as a film or as droplets, therefore impeding further release of first fluid or disrupting the kinetics of the release.

Thus, it may be desirable to actively remove adsorbed first fluid from the surface of the rock sample 2. Although this may be done in a continuous manner, it is preferable to intermittently, e.g. periodically, perform such removal, for instance once an hour, or once every 12 hours, or once a day. For example, the surface of the rock sample 2 may be scraped by the scrapers 6. The removal may for instance be performed before measuring the amount of released first fluid.

The second fluid and the rock sample 2 in the cell 1 may be maintained at the temperature of the reservoir from which the rock sample 2 was extracted. In particular, they may be maintained at a temperature from 25 to 150° C., preferably from 40 to 120° C. and more preferably from 60 to 110° C.

Part or all of the fluid output from the cell 1 via the output line 10 may be analyzed; for example, the pH of the fluid, or its salinity, or its chemical composition, may be determined in order to assess how the incoming fluid interacted with the sample.

The method of the invention makes it possible to successively test two, or more than two, second fluids. In this case, the method as described above is implemented for a certain period of time with one second fluid. Then, the source 8 of second fluid is modified, another second fluid is fed to the cell 1 and progressively replaces the previous second fluid, and the method is implemented for another period of time with the other second fluid. This can be repeated with yet further second fluids, if desired.

As described above, the first fluid may be oil and the second fluid may be an aqueous solution; or the first fluid may be an aqueous solution and the second fluid may be oil.

The aqueous solution may comprise water, salts, and possibly chemical additives such as surfactants. The aqueous solution may be seawater, or produced water collected from a production well, or any solution simulating the above. When use is made of at least two aqueous solutions as successive second fluids, they may differ by their pH, salinity and/or chemical additives. In such a case, the initial second fluid may be used until a plateau of first fluid (oil) release is reached; then another second fluid is used to promote an additional release of first fluid (oil); etc.

The invention makes it possible to switch from one fluid to the next without damaging or polluting the sample by withdrawing it from the test cell and exposing it to the ambient air.

A complete analysis of a rock sample may include the following stages.

First, the rock sample may be prepared.

Second, spontaneous imbibition of the rock sample may be performed using the method described above, wherein the first fluid is oil and the second fluid is an aqueous solution (or the second fluids are aqueous solutions); at the end of this stage, a total volume of oil spontaneously released from the sample ($V_{SO}$) may be obtained.

Third, forced imbibition of the rock sample may be performed, by e.g. withdrawing the rock sample from the apparatus described above, and subjecting it to centrifugation in the presence of aqueous solution; at the end of this stage, a total volume of oil forcibly released from the sample ($V_{FO}$) may be obtained.

An index of water wettability ($I_{WW}$) may then be obtained as follows: $I_{WW}=V_{SO}/(V_{SO}+V_{FO})$.

Fourth, spontaneous drainage of the same rock sample may be performed, optionally still using the method described above, wherein the first fluid is an aqueous solution and the second fluid is oil; at the end of this stage, a total volume of aqueous solution spontaneously released from the sample ($V_{SW}$) may be obtained.

Fifth, forced drainage of the rock sample may be performed, by e.g. subjecting it to centrifugation in the presence of oil; at the end of this stage, a total volume of aqueous solution forcibly released from the sample ($V_{FW}$) may be obtained.

An index of oil wettability (low) may then be obtained as follows: $I_{OW}=V_{SW}/(V_{SW}+V_{FW})$.

The Amott index $I_A$ may then be obtained as follows: $I_A=I_{OW}-I_{WW}$.

The method of the invention may include only the second stage, or only the first and second stages, or only the second and third stages, or only the first, second and third stages, or only the fourth stage, or only the fourth and fifth stages, or all five stages described above.

The first stage of preparing the rock sample may include involve cleaning the rock sample, draining the rock sample, and conditioning the rock sample. Said preparation is useful since a sample extracted from a reservoir is usually not in its native condition and is polluted by a number of contaminants, such as drilling fluids and the like.

The preparation may more specifically comprise:
cleaning the sample with one or more solvents so as to remove hydrocarbons and other fluids from the sample;
evaporating the solvents by e.g. subjecting the sample to a vacuum, or by any other form of drying;
saturating the sample with brine;

draining the brine from the sample and introducing oil (such as e.g. neutral oil, namely white mineral oil) into the sample, by centrifuging the sample immersed in said oil;

conditioning the sample in a cell to replace said oil by reservoir oil ("dead oil"), preferably at the temperature of the reservoir, and preferably under a slight flow rate of oil.

The invention claimed is:

1. A method of analyzing a rock sample, comprising:
placing a rock sample containing a first fluid into a cell;
feeding the cell with at least one second fluid and withdrawing said second fluid from the cell, leaving the rock sample immersed in the second fluid;
measuring an amount of first fluid spontaneously released from the rock sample; and
wherein the first fluid naturally exits the rock sample without being forcibly pushed out of the rock sample by a pressure differential between one end of the rock sample and another end of the rock sample.

2. The method of claim 1, wherein the second fluid is continuously fed to the cell and continuously withdrawn from the cell.

3. The method of claim 1, wherein use is made of a single second fluid.

4. The method of claim 1, which comprises successively feeding the cell with a second fluid and withdrawing said second fluid from the cell, and then feeding the cell with another second fluid and withdrawing said other second fluid from the cell.

5. The method of claim 1, wherein the first fluid spontaneously released from the rock sample is collected in a collection area of the cell and the volume of first fluid in the collection area is measured.

6. The method of claim 1, wherein the first fluid in the collection area has a surface which is in contact with a gas, and the position of the first fluid in the collection area is set at a target position by adjusting gas pressure.

7. The method of claim 1, wherein the second fluid or each second fluid is an aqueous solution, and the first fluid is oil.

8. The method of claim 1, wherein the second fluid is oil, and the first fluid is an aqueous solution.

9. The method of claim 1, which further comprises removing adsorbed first fluid at the surface of the rock sample, when the rock sample is immersed in the second fluid.

10. The method of claim 1, which further comprises scraping the rock sample inside the cell.

11. The method of claim 1, wherein the second fluid and rock sample in the cell are maintained at an absolute pressure of from 2 to 10 bar.

12. The method of claim 1, wherein the second fluid and rock sample in the cell are maintained at a temperature of from 40 to 120° C.

13. An apparatus for analyzing a rock sample containing a first fluid, comprising:
a cell for accommodating the rock sample;
a feed line for feeding the cell with a second fluid;
an output line for withdrawing said second fluid from the cell;
a measurement system for measuring the amount of first fluid spontaneously released from the rock sample; and
wherein the collection area is located in a top part of the cell and the apparatus further comprises a gas line for brining gas in contact with the first fluid in the collection area, the gas line being provided with gas pressure adjustment equipment.

14. The apparatus of claim 13, comprising a pressure regulation system for maintaining pressure in the cell and rock sample at a predetermined level.

15. The apparatus of claim 13, wherein the cell comprises a collection area, and the measurement system is configured for measuring a volume of first fluid in the collection area.

16. The apparatus of claim 13, wherein the cell comprises a first portion for accommodating the rock sample and a second portion as the collection area, wherein the second portion is a generally vertical tubular portion, having a reduced horizontal cross-section relative to the first portion.

17. The apparatus of claim 13, wherein the collection area is located in a bottom part of the cell.

18. The apparatus of claim 13, which comprises a holder for the rock sample in the cell.

19. The apparatus of claim 13, which comprises one more scrapers for scraping the rock sample in the cell.

20. An apparatus for analyzing a rock sample containing a first fluid, comprising:
a cell for accommodating the rock sample;
a feed line for feeding the cell with a second fluid;
an output line for withdrawing said second fluid from the cell; and
a measurement system for measuring the amount of first fluid spontaneously released from the rock sample;
the apparatus comprising one or more scrapers for scraping the rock sample in the cell.

* * * * *